United States Patent
Sabesan

(10) Patent No.: US 9,056,195 B2
(45) Date of Patent: Jun. 16, 2015

(54) OPTIMIZATION OF CRANIAL NERVE STIMULATION TO TREAT SEIZURE DISORDERSE DURING SLEEP

(71) Applicant: Cyberonics, Inc., Houston, TX (US)

(72) Inventor: Shivkumar Sabesan, Houston, TX (US)

(73) Assignee: CYBERONICS, INC., Houston, TX (US)

( * ) Notice: Subject to any disclaimer, the term of this patent is extended or adjusted under 35 U.S.C. 154(b) by 14 days.

(21) Appl. No.: 13/834,523

(22) Filed: Mar. 15, 2013

(65) Prior Publication Data

US 2014/0277255 A1    Sep. 18, 2014

(51) Int. Cl.
*A61N 1/36* (2006.01)
*A61N 1/05* (2006.01)

(52) U.S. Cl.
CPC .......... *A61N 1/0529* (2013.01); *A61N 1/36064* (2013.01)

(58) Field of Classification Search
CPC ........... A61N 1/36053; A61N 1/36078; A61N 1/36017; A61N 1/36135; A61N 1/3611; A61N 1/3601; A61N 1/36025; A61N 1/36071; A61N 1/0551; A61N 1/0517; A61B 5/4818; A61B 5/0476
USPC .......................................................... 607/45
See application file for complete search history.

(56) References Cited

U.S. PATENT DOCUMENTS

| | | | |
|---|---|---|---|
| 4,702,254 A | 10/1987 | Zabara | |
| 4,867,164 A | 9/1989 | Zabara | |
| 4,920,979 A | 5/1990 | Bullara | |
| 4,979,511 A | 12/1990 | Terry, Jr. | |
| 5,012,411 A | 4/1991 | Policastro et al. | |
| 5,025,807 A | 6/1991 | Zabara | |
| 5,081,987 A | 1/1992 | Nigam | |
| 5,137,020 A | 8/1992 | Wayne et al. | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,215,089 A | 6/1993 | Baker, Jr. | |
| 5,222,494 A | 6/1993 | Baker, Jr. | |
| 5,231,988 A | 8/1993 | Wernicke et al. | |
| 5,235,980 A | 8/1993 | Varrichio et al. | |
| 5,237,991 A | 8/1993 | Baker, Jr. et al. | |
| 5,263,480 A | 11/1993 | Wernicke et al. | |
| 5,269,302 A | 12/1993 | Swartz et al. | |
| 5,269,303 A | 12/1993 | Wernicke et al. | |
| 5,299,569 A | 4/1994 | Wernicke et al. | |
| 5,304,206 A | 4/1994 | Baker, Jr. et al. | |
| 5,330,507 A | 7/1994 | Schwartz | |

(Continued)

OTHER PUBLICATIONS

Borovikova, L.V. et al., "Vagus Nerve Stimulation Attenuates the Systemic Inflammatory Response to Endotoxin," Letters to Nature, Nature, vol. 405, May 25, 2000, pp. 458-462.

(Continued)

*Primary Examiner* — Carl H Layno
*Assistant Examiner* — Erin Piateski
(74) *Attorney, Agent, or Firm* — Cyberonics, Inc.

(57) ABSTRACT

A method includes determining sleep cycle information related to a sleep cycle of a patient based on body parameter data. The method also includes adjusting a cranial nerve stimulation parameter based on the sleep cycle information.

9 Claims, 9 Drawing Sheets

(56) References Cited

U.S. PATENT DOCUMENTS

| | | |
|---|---|---|
| 5,330,515 A | 7/1994 | Rutecki et al. |
| 5,335,657 A * | 8/1994 | Terry et al. .................. 607/45 |
| 5,458,625 A | 10/1995 | Kendall |
| 5,522,862 A | 6/1996 | Testerman et al. |
| 5,531,778 A | 7/1996 | Maschino et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,435 A | 2/1997 | Quy |
| 5,611,350 A | 3/1997 | John |
| 5,690,681 A | 11/1997 | Geddes et al. |
| 5,690,688 A | 11/1997 | Noren et al. |
| 5,700,282 A | 12/1997 | Zabara |
| 5,707,400 A | 1/1998 | Terry, Jr. et al. |
| 5,720,771 A | 2/1998 | Snell |
| 5,743,860 A | 4/1998 | Hively et al. |
| 5,814,092 A | 9/1998 | King |
| 5,913,882 A | 6/1999 | King |
| 5,916,239 A | 6/1999 | Geddes et al. |
| 5,928,272 A | 7/1999 | Adkins et al. |
| 5,995,868 A | 11/1999 | Dorfmeister et al. |
| 6,016,449 A | 1/2000 | Fischell et al. |
| 6,018,682 A | 1/2000 | Rise |
| 6,041,258 A | 3/2000 | Cigaina et al. |
| 6,061,593 A | 5/2000 | Fischell et al. |
| 6,073,048 A | 6/2000 | Kieval et al. |
| 6,104,956 A | 8/2000 | Naritoku et al. |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,240,316 B1 | 5/2001 | Richmond et al. |
| 6,269,270 B1 | 7/2001 | Boveja |
| 6,304,775 B1 | 10/2001 | Iasemidis et al. |
| 6,324,421 B1 | 11/2001 | Stadler et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,788 B2 | 3/2002 | Boveja |
| 6,366,814 B1 | 4/2002 | Boveja et al. |
| 6,459,936 B2 | 10/2002 | Fischell et al. |
| 6,473,639 B1 | 10/2002 | Fischell et al. |
| 6,473,644 B1 | 10/2002 | Terry, Jr. et al. |
| 6,484,132 B1 | 11/2002 | Hively et al. |
| 6,505,074 B2 | 1/2003 | Boveja et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,606,523 B1 | 8/2003 | Jenkins |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,658,294 B1 | 12/2003 | Zadeh et al. |
| 6,662,052 B1 | 12/2003 | Sarwal et al. |
| 6,668,191 B1 | 12/2003 | Boveja |
| 6,671,555 B2 | 12/2003 | Gielen et al. |
| 6,671,556 B2 | 12/2003 | Osorio et al. |
| 6,681,003 B2 | 1/2004 | Linder et al. |
| 6,684,104 B2 | 1/2004 | Gordon et al. |
| 6,684,105 B2 | 1/2004 | Cohen et al. |
| 6,708,064 B2 | 3/2004 | Rezai |
| 6,721,603 B2 | 4/2004 | Zabara et al. |
| 6,760,626 B1 | 7/2004 | Boveja |
| 6,764,498 B2 | 7/2004 | Mische |
| 6,768,969 B1 | 7/2004 | Nikitin et al. |
| 6,819,956 B2 | 11/2004 | DiLorenzo |
| 6,904,390 B2 | 6/2005 | Nikitin et al. |
| 6,920,357 B2 | 7/2005 | Osorio et al. |
| 6,922,592 B2 | 7/2005 | Thompson et al. |
| 6,934,580 B1 | 8/2005 | Osorio et al. |
| 6,944,501 B1 | 9/2005 | Pless |
| 6,959,215 B2 | 10/2005 | Gliner et al. |
| 6,961,618 B2 | 11/2005 | Osorio et al. |
| 7,006,872 B2 | 2/2006 | Gielen et al. |
| 7,043,305 B2 | 5/2006 | KenKnight et al. |
| 7,050,856 B2 | 5/2006 | Stypulkowski |
| 7,054,792 B2 | 5/2006 | Frei et al. |
| 7,076,288 B2 | 7/2006 | Skinner |
| 7,079,977 B2 | 7/2006 | Osorio et al. |
| 7,134,996 B2 | 11/2006 | Bardy |
| 7,146,211 B2 | 12/2006 | Frei et al. |
| 7,149,572 B2 | 12/2006 | Frei et al. |
| 7,149,581 B2 | 12/2006 | Goedeke |
| 7,156,808 B2 | 1/2007 | Quy |
| 7,156,809 B2 | 1/2007 | Quy |
| 7,164,941 B2 | 1/2007 | Misczynski et al. |
| 7,167,743 B2 | 1/2007 | Heruth et al. |
| 7,167,750 B2 | 1/2007 | Knudson et al. |
| 7,171,271 B2 | 1/2007 | Koh et al. |
| 7,188,053 B2 | 3/2007 | Nikitin et al. |
| 7,228,167 B2 | 6/2007 | Kara et al. |
| 7,231,254 B2 | 6/2007 | DiLorenzo |
| 7,236,831 B2 | 6/2007 | Firlik et al. |
| 7,242,983 B2 | 7/2007 | Frei et al. |
| 7,254,439 B2 | 8/2007 | Misczynski et al. |
| 7,263,467 B2 | 8/2007 | Sackellares et al. |
| 7,265,676 B2 | 9/2007 | Gordon et al. |
| 7,277,758 B2 | 10/2007 | DiLorenzo |
| 7,280,867 B2 | 10/2007 | Frei et al. |
| 7,282,030 B2 | 10/2007 | Frei et al. |
| 7,292,890 B2 | 11/2007 | Whitehurst et al. |
| 7,295,881 B2 | 11/2007 | Cohen et al. |
| 7,305,268 B2 | 12/2007 | Gliner et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,340,302 B1 | 3/2008 | Falkenberg et al. |
| 7,353,064 B2 | 4/2008 | Gliner et al. |
| 7,366,572 B2 | 4/2008 | Heruth et al. |
| 7,373,199 B2 | 5/2008 | Sackellares et al. |
| 7,389,144 B1 | 6/2008 | Osorio et al. |
| 7,401,008 B2 | 7/2008 | Frei et al. |
| 7,403,820 B2 | 7/2008 | DiLorenzo |
| 7,483,747 B2 | 1/2009 | Gliner et al. |
| 7,894,890 B2 * | 2/2011 | Sun et al. .................. 600/544 |
| 2002/0072782 A1 | 6/2002 | Osorio et al. |
| 2002/0099417 A1 | 7/2002 | Naritoku et al. |
| 2002/0151939 A1 | 10/2002 | Rezai |
| 2002/0188214 A1 | 12/2002 | Misczynski et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138647 A1 | 7/2004 | Osorio et al. |
| 2004/0138711 A1 | 7/2004 | Osorio et al. |
| 2004/0158119 A1 | 8/2004 | Osorio et al. |
| 2004/0199212 A1 | 10/2004 | Fischell et al. |
| 2005/0124901 A1 | 6/2005 | Misczynski et al. |
| 2005/0143786 A1 | 6/2005 | Boveja |
| 2005/0148893 A1 | 7/2005 | Misczynski et al. |
| 2005/0148895 A1 | 7/2005 | Misczynski et al. |
| 2005/0154425 A1 | 7/2005 | Boveja et al. |
| 2005/0177192 A1 | 8/2005 | Rezai et al. |
| 2005/0187590 A1 | 8/2005 | Boveja et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0277998 A1 | 12/2005 | Tracey et al. |
| 2006/0009815 A1 | 1/2006 | Boveja et al. |
| 2006/0155495 A1 | 7/2006 | Osorio et al. |
| 2006/0167497 A1 | 7/2006 | Armstrong et al. |
| 2006/0173493 A1 | 8/2006 | Armstrong et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0293720 A1 | 12/2006 | DiLorenzo |
| 2007/0027486 A1 | 2/2007 | Armstrong |

(56) References Cited

U.S. PATENT DOCUMENTS

| | | | |
|---|---|---|---|
| 2007/0088404 A1 | 4/2007 | Wyler et al. | |
| 2007/0100278 A1 | 5/2007 | Frei et al. | |
| 2007/0100392 A1 | 5/2007 | Maschino et al. | |
| 2007/0123758 A1* | 5/2007 | Miesel et al. | 600/301 |
| 2007/0208212 A1 | 9/2007 | DiLorenzo | |
| 2007/0213785 A1 | 9/2007 | Osorio et al. | |
| 2007/0233192 A1 | 10/2007 | Craig | |
| 2007/0239210 A1 | 10/2007 | Libbus et al. | |
| 2007/0244407 A1 | 10/2007 | Osorio | |
| 2007/0282177 A1 | 12/2007 | Pilz | |
| 2008/0033508 A1 | 2/2008 | Frei et al. | |
| 2008/0064934 A1 | 3/2008 | Frei et al. | |
| 2008/0081941 A1* | 4/2008 | Tononi | 600/14 |
| 2008/0103548 A1 | 5/2008 | Fowler et al. | |
| 2008/0119900 A1 | 5/2008 | DiLorenzo | |
| 2008/0195166 A1* | 8/2008 | Sun et al. | 607/18 |
| 2008/0208285 A1 | 8/2008 | Fowler et al. | |
| 2008/0234598 A1 | 9/2008 | Snyder et al. | |
| 2008/0234785 A1* | 9/2008 | Nakayama et al. | 607/62 |
| 2010/0087701 A1* | 4/2010 | Berka et al. | 600/27 |
| 2011/0112381 A1* | 5/2011 | Sun et al. | 600/300 |
| 2011/0295083 A1* | 12/2011 | Doelling et al. | 600/301 |
| 2012/0277618 A1* | 11/2012 | Giftakis et al. | 600/544 |

OTHER PUBLICATIONS

Chakravarthy, N. et al., "Controlling Synchronization in a Neuron-Level Population Model," International Journal of Neural Systems, vol. 17, No. 2, 2007, pp. 123-138.

Chen, C. et al., "Vagal Efferent Fiber Stimulation Ameliorates Pulmonary Microvascular Endothelial Cell Injury by Downregulating Inflammatory Responses," Inflammation, vol. 36, No. 6, Dec. 2013, pp. 1567-1575.

Dodrill, C.B. et al., "Effects of Vagal Nerve Stimulation on Cognition and Quality of Life in Epilepsy,"Epilepsy & Behavior, vol. 2, Issue 1, 2001, pp. 46-53.

Frei, M.G. et al., "Left Vagus Nerve Stimulation with the Neurocybernetic Prosthesis Has Complex Effects on Heart Rate and on Its Variability in Humans," Epilepsia, vol. 42, No. 8, 2001, pp. 1007-1016.

Iasemidis, L.D. et al., "Spatiotemporal Transition to Epileptic Seizures: A Nonlinear Dynamical Analysis of Scalp and Intracranial EEG Recordings," Spatiotemporal Models in Biological and Artificial Systems, IOS Press, 1997, pp. 81-88.

Jaseja, H., "Vagal Nerve Stimulation Technique: Enhancing Its Efficacy and Acceptability by Augmentation with Auto Activation and Deactivation Mode of Operation," Medical Hypotheses, vol. 63, Issue 1, 2004, pp. 76-79.

Kucera, M., "'Active Air' Inhalation Therapy: Autonomic Regulation Mechanisms with Use of Heart Rate Variability Analysis," Explore! vol. 16, No. 2, 2007, 3 pages.

Malow, B.A. et al., "Vagus Nerve Stimulation Reduces Daytime Sleepiness in Epilepsy Patients," Neurology, vol. 57, Issue 5, 2001, pp. 879-884.

Valdes-Cruz, A. et al., "Chronic Stimulation of the Cat Vagus Nerve Effect on Sleep and Behavior," Progress in Neuro-Psychopharmacology & Biological Psychiatry, vol. 26, Issue 1, 2002, pp. 113-118.

Zabara, J., "Neuroinhibition in the Regulation of Emesis," Space Life Sciences, vol. 3, Issue 3, 1972, pp. 282-292.

* cited by examiner

OPTIMIZATION OF CRANIAL NERVE STIMULATION TO TREAT SEIZURE DISORDERSE DURING SLEEP

FIELD OF THE DISCLOSURE

The present disclosure is generally related to cranial nerve stimulation to treat seizure disorders

BACKGROUND

Sleep may be characterized by four stages, stage one sleep, stage two sleep, stage three sleep, and rapid eye movements (REM) stage sleep. The four stages may form a sleep cycle. Typically in a sleep cycle, a person experiences the four stages in sequence (e.g., stage one sleep→stage two sleep→stage three sleep→REM stage sleep). A person may experience several sleep cycles during a sleep period (e.g., during a night). The number of sleep cycles a person experiences per sleep period depends on the age of the person, duration of the sleep period, and other factors.

Neurological disorders (e.g., a seizure disorder or depression) may interfere with a person's sleep quality. For example, a patient with a seizure disorder may experience seizures during sleep. The seizures experienced during sleep may affect the patient's sleep quality. When the patient has a seizure during sleep, the seizure may awaken the patient prematurely from a particular sleep cycle. The patient does not finish the particular sleep cycle and has to fall back asleep to start another sleep cycle. Thus, the patient experiences sleep deprivation.

SUMMARY

Seizures that occur during sleep may deprive a patient of sleep. In some patients, seizures are more common during stage 2 sleep. When a patient experiences a seizure during stage 2 sleep, instead of transitioning to stage 3 sleep, the seizure may awaken the patient. Thus, the patient may not get an appropriate amount of stage 3 sleep and/or REM stage sleep and may experience sleep deprivation. When the patient goes back to sleep, the patient may start from stage 1 sleep of a new sleep cycle or may stay in stage 3 sleep without transitioning to REM stage sleep. Sleep deprivation may have negative physiological effects on the patient, such as memory impairment, mental impairment, etc.

Systems and methods described herein may improve sleep quality of a patient with a seizure disorder. For example, an implantable medical device (IMD) may determine sleep cycle information related to one or more sleep cycles of a patient by monitoring body parameter data of the patient. The sleep cycle information may include a particular sleep stage, a sleep stage transition, an amount of time the patient spends in one or more sleep stages during a sleep cycle and/or multiple sleep cycles, or a combination thereof. Based on the sleep cycle information, the IMD may apply cranial nerve stimulation (CNS) to the patient to help the patient complete the four stages of a sleep cycle. The IMD may also, or in the alternative, adjust one or more CNS parameters based on the sleep cycle information to treat one or more seizure disorders. CNS may include vagus nerve stimulation (VNS), trigeminal nerve stimulation (TNS), stimulation of other cranial nerves, or a combination thereof.

To illustrate, the IMD may determine a sleep stage of the patient and may monitor sleep stage transitions. Empirical data has shown that seizures may occur more frequently and may be more severe during stage 2 sleep and may occur less frequently during stage 3 sleep and REM stage sleep. When the IMD determines that the patient is in stage 2 sleep, the IMD may adjust a CNS parameter to drive the patient toward stage 3 sleep and subsequently toward REM stage sleep to complete a sleep cycle. When the patient reaches stage 3 sleep and/or REM stage sleep of a sleep cycle, the likelihood of a seizure occurring during the sleep cycle may be reduced. The patient may get an increased amount of sleep in each sleep cycle as compared to an amount of sleep of a patient awakened by seizures. Thus, the patient may have improved sleep quality and may also experience fewer seizures during sleep.

The IMD may also, or in the alternative, determine information regarding efficacy of a CNS therapy based on the sleep cycle information. For example, the IMD or an external device (e.g., a computing device) may compare sleep cycle information of the patient before applying CNS therapy to sleep cycle information of the patient during and/or after the CNS therapy. One or more CNS parameters of the CNS therapy may be adjusted based on the comparison to increase the efficacy of the CNS therapy.

In a particular embodiment, a method includes determining sleep cycle information related to a sleep cycle of a patient based on body parameter data. The method also includes adjusting a cranial nerve stimulation parameter based on the sleep cycle information.

In another particular embodiment, a device includes a processor that is configured to determine sleep cycle information related to a sleep cycle of a patient based on body parameter data. The processor is further configured to adjust a cranial nerve stimulation parameter based on the sleep cycle information. The apparatus also includes a memory coupled to the processor. The apparatus further includes a therapy delivery unit configured to apply cranial nerve stimulation based on the sleep cycle information.

In another particular embodiment, a non-transitory computer-readable medium includes instructions executable by a processor. The instructions may be executable by the processor to determine sleep cycle information related to a sleep cycle of a patient based on body parameter data and to adjust a cranial nerve stimulation parameter based on the sleep cycle information.

DETAILED DESCRIPTION

Figure 1:
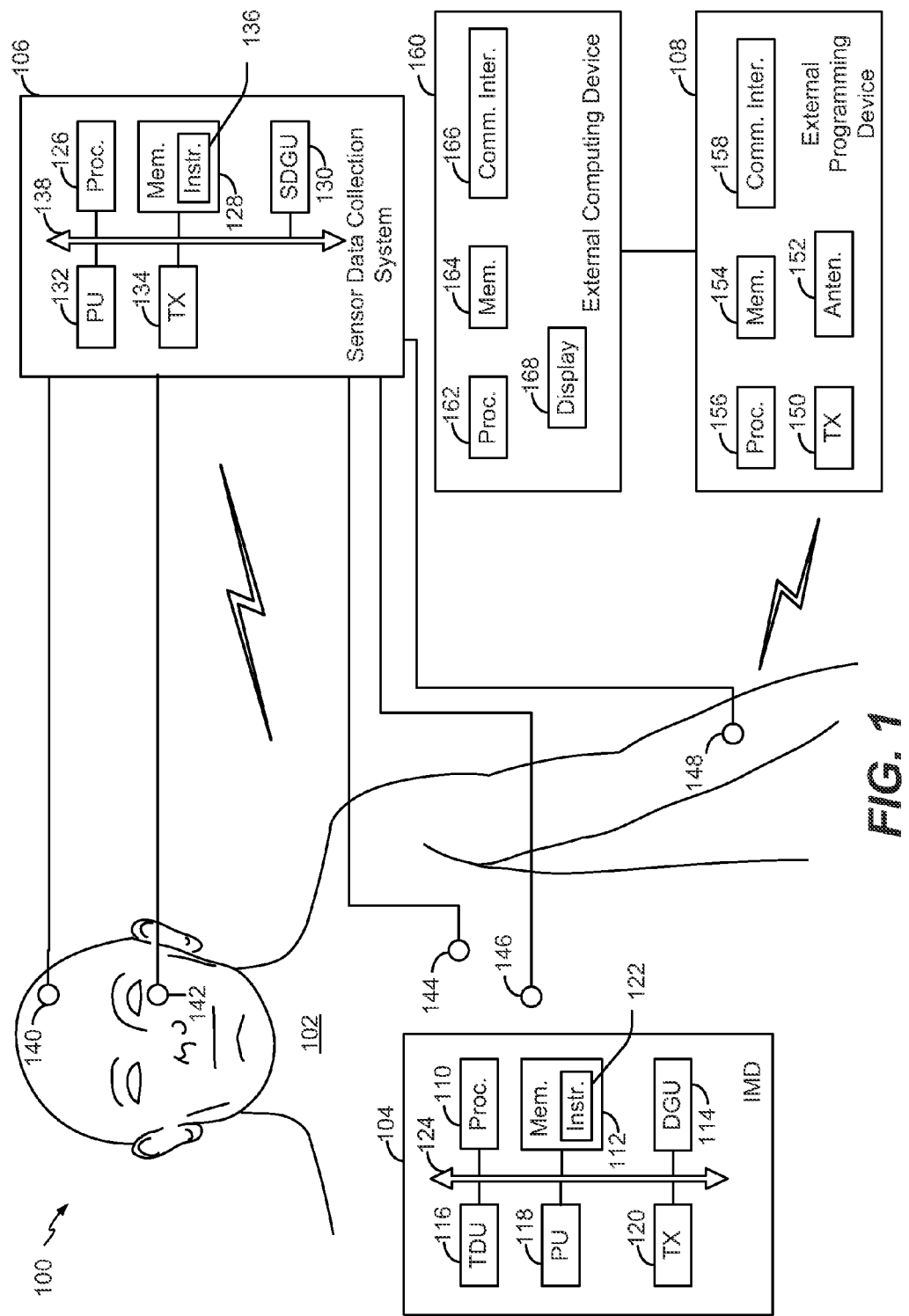
FIG. 1 is a block diagram of a particular embodiment of a system that uses cranial nerve stimulation to treat seizures during sleep.

Referring to FIG. 1, a block diagram of a system 100 that uses cranial nerve stimulation (CNS) to treat seizures of a patient 102 (e.g., an epilepsy patient) during sleep is shown according an exemplary embodiment. CNS may include vagus nerve stimulation (VNS), trigeminal nerve stimulation (TNS), stimulation of other cranial nerves, or a combination thereof. The system 100 may include an implantable medical device (IMD) 104, a sensor data collection system 106, and/or an external programming device 108. The IMD 104 may include a processor 110, a memory 112, a data gathering unit (DGU) 114, a therapy delivery unit (TDU) 116, a power unit (PU) 118, a transceiver (TX) 120, a system bus 124, other components (not shown), or a combination thereof. The processor 110 may be a single processor of the IMD 104 or multiple processors of the IMD 104. The memory 112 may include instructions 122 that are executable by the processor 110 to perform or control various functions of the IMD 104.

The data gathering unit 114 may gather data related to an operational state of the IMD 104 (e.g., a charge state of the power unit 118), data related to therapy provided to the patient 102, body parameter data corresponding to one or more body parameters of the patient 102, or a combination thereof. Data gathered by the data gathering unit 114 may be used to control therapy provided to the patient 102, may be transmitted to an external device, may be stored in the memory 112, transmitted to a server (e.g., a cloud), or a combination thereof.

The therapy delivery unit 116 may be configured to provide therapy to the patient 102. For example, the therapy delivery unit 116 may provide electrical stimulation (via one or more electrodes (not shown)) to tissue of the patient 102. The therapy delivery unit 116 may provide electrical stimulation to a cranial nerve (e.g., the vagus nerve, the trigeminal nerve, etc.) of the patient 102. As another example, the therapy delivery unit 116 may include a drug pump that delivers a drug or drugs to the patient 102. Therapy provided by the therapy delivery unit 116 may be controlled by the processor 110 based on a treatment program.

The power unit 118 may provide electrical power to components of the IMD 104. For example, the power unit 118 may include a battery or a capacitor. The transceiver 120 may enable the IMD 104 to communicate with other devices, such as the sensor data collection system 106 and the external programming device 108. The processor 110, the memory 112, the data gathering unit 114, the therapy delivery unit 116, the power storage unit 118, the transceiver 120, other components of the IMD 104, or a combination thereof, may be connected via the system bus 124.

The sensor data collection system 106 may include a processor 126, a memory 128, a sensor data gathering unit (SDGU) 130, a power unit (PU) 132, a transceiver (TX) 134, a system bus 138, other components (not shown), or a combination thereof. The processor 126 may be a single processor of the sensor data collection system 106 or multiple processors of the sensor data collection system 106. The memory 128 may include instructions 136 that are executable by the processor 126 to perform or control various functions of the sensor data collection system 106.

The sensor data gathering unit 130 may be configured to collect body parameter data from sensors placed on or implanted within tissue of the patient 102. For example, an electroencephalography (EEG) sensor 140, an electrooculography (EOG) sensor 142, an electrocardiography (ECG) sensor 144, an electromyography (EMG) sensor 146, an accelerometer 148, an impedance monitoring unit, a respiration sensor (e.g., on the chest or nose), a blood oxygenation sensor, an acoustic sensor (e.g., to measure snoring), other sensors, or a combination thereof, may be placed on or implanted within tissue of the patient 102 to sense the body parameter data of the patient 102. The body parameter data may include EEG data, EOG data, ECG data, EMG data, accelerometer data, or a combination thereof. The sensor data gathering unit 130 may receive the body parameter data via respective wired or wireless connections to the EEG sensor 140, the EOG sensor 142, the ECG sensor 144, the EMG sensor 146, the accelerometer 148, the other sensors, or a combination thereof.

The power unit 132 may be configured to provide electrical power to components of the sensor data collection system 106. For example, the power unit 132 may include a battery, a capacitor, a power supply coupled to an external source (e.g., alternate current (AC) power), or a combination thereof. The power unit 132 may be configured to selectively power on and off one or more of the various sensors on demand. The transceiver 134 may be configured to enable the sensor data collection system 106 to communicate with other devices, such as the IMD 104, the external programming device 108, or both. The processor 126, the memory 128, the sensor data gathering unit 130, the power unit 132, and the transceiver 134 may be connected via the system bus 138.

The external programming device 108 may include a transceiver (TX) 150 and an antenna 152. The transceiver 150 may be configured to communicate (e.g., transmit data, receive data, or a combination thereof) via the antenna 152 with the IMD 104, the sensor data collection system 106, or both. For example, the external programming device 108 may send program data, such as therapy parameter data to the IMD 104 using wireless signals. The program data may be stored at a memory 154 of the external programming device 108, may be received from an external computing device 160, or both. In a particular embodiment, the external programming device 108 may also include a processor 156 and/or a communication interface 158 to communicate with the external computing device 160.

The external computing device 160 may include a processor 162, a memory 164, a communication interface 166, a display 168, other components (not shown), or a combination thereof. The external computing device 160 may receive data from the external programming device 108, the sensor data collection system 106, the IMD 104, or a combination thereof, via the communication interface 166 and may store the data in the memory 164. The external computing device 160 may provide an interface (e.g., via the display 168) to the patient 102 and/or a health care provider to see the stored data. The stored data may be used to facilitate determining information regarding efficacy of a therapy.

During operation, when the patient 102 is asleep, the sensor data collection system 106 may collect the body parameter data from the EEG sensor 140, the EOG sensor 142, the ECG sensor 144, the EMG sensor 146, the accelerometer 148, another sensor, or a combination thereof. The sensor data collection system 106 may communicate the body parameter data to the IMD 104 occasionally (e.g., periodically or in response to detection of an event) or continuously. For example, the sensor data collection system 106 may communicate the body parameter data to the IMD 104 in real time (as soon as the sensor data collection system 106 receives the body parameter data and processes the body parameter data for transmission). Based on the body parameter data, the IMD 104, the sensor data collection system 106, the external programming device 108, the external computing device 160, or a combination thereof, may determine sleep cycle information related to a sleep cycle of the patient 102.

The IMD 104, the sensor data collection system 106, the external programming device 108, the external computing device 160, or a combination thereof, may evaluate the sleep cycle information to determine a sleep stage (e.g., stage 1 sleep, stage 2 sleep, stage 3 sleep, and/or REM stage sleep) of the patient 102. The IMD 104, the sensor data collection system 106, the external programming device 108, the external computing device 160, or a combination thereof, may also, or in the alternative, evaluate the sleep cycle information to detect a sleep stage transition. For example, the sleep stage transition may include a transition from stage 1 sleep to stage 2 sleep, a transition from stage 2 sleep to stage 3 sleep, a transition from stage 3 sleep to REM stage sleep, a transition from REM stage sleep to stage 1 sleep, a transition from one of stage 1 sleep, stage 2 sleep, stage 3 sleep, and/or REM stage sleep to wakefulness, or a combination thereof.

The IMD 104, the sensor data collection system 106, the external programming device 108, the external computing device 160, or a combination thereof, may also, or in the alternative, evaluate the sleep cycle information to determine an amount of time the patient 102 spends in one or more sleep stages during a sleep cycle (e.g., a sleep quota). The IMD 104, the sensor data collection system 106, the external programming device 108, the external computing device 160, or a combination thereof, may also, or in the alternative, evaluate the sleep cycle information to determine an amount of time the patient 102 has spent in one or more sleeps stages during a sleep period. The sleep period may include multiple sleep cycles. For example, based on body parameter data, the IMD 104, the sensor data collection system 106, the external programming device 108, the external computing device 160, or a combination thereof, may monitor the sleep quota and/or the amount of time the patient 102 has spent in one or more sleep stages during the sleep period.

Based on the sleep cycle information, the IMD 104, the sensor data collection system 106, the external programming device 108, the external computing device 160, or a combination thereof, may adjust one or more CNS parameters to adjust the CNS applied to the patient 102. The one or more CNS parameters may include a pulse width, an output current, an output voltage, a pulse frequency, a burst frequency, an interburst interval, a duty cycle, an on-time, an off-time, a frequency sweep, or a combination thereof. The one or more CNS parameters may be used to generate stimulation signals applied to a cranial nerve of the patient 102. For example, when the sleep cycle information indicates a transition from stage 2 sleep toward wakefulness (e.g., a transition from stage 2 sleep toward wakefulness caused by a seizure), the IMD 104 may adjust the CNS parameter such that synchrony of brainwaves of the patient 102 is increased so that the CNS may drive the patient toward stage 3. In some embodiments, the IMD 104 may adjust the CNS parameter such that the CNS may drive the patient 102 toward stage 3 sleep when the sleep cycle information indicates a transition from stage 1 sleep to stage 2 sleep, a current sleep stage is stage 2 sleep, a predetermined amount of time has been spent in stage 2 sleep during a sleep cycle, or a combination thereof. Applying CNS to drive the patient 102 toward stage 3 sleep to continue the sleep cycle may reduce seizures as empirical data has shown that seizures rarely occur in stage 3 sleep or REM stage sleep. Furthermore, the patient 102 may have improved sleep quality as the patient 102 continues to sleep instead of waking up. Adjusting the CNS parameter such that synchrony of the brainwaves of the patient 102 is either increased or decreased is described in more detail with reference to FIG. 4.

As another example, when the sleep cycle information indicates that an amount of time the patient 102 has spent in REM stage sleep during a sleep period is less than a first threshold, the IMD 104 may adjust the CNS parameter such that the CNS may drive the patient 102 toward REM stage sleep (e.g., remaining in REM stage sleep until the patient 102 has spent an amount of time in REM stage sleep equal to the threshold).

As another example, when the sleep cycle information indicates that an amount of time the patient 102 has spent in stage 3 sleep during a sleep period is less than a second threshold, the IMD 104 may adjust the CNS parameter such that the CNS may drive the patient 102 toward stage 3 sleep (e.g., remaining in stage 3 sleep until the patient 102 has spent an amount of time in stage 3 sleep equal to the second threshold). An amount of time the patient 102 spent in stage 1 sleep may also be compared to a third threshold. An amount of time the patient 102 spent in stage 2 sleep may be compared to a fourth threshold. The first, second, third, and fourth thresholds may correspond to an amount of time, or a portion thereof, that a healthy person may spend in REM stage sleep, stage 3 sleep, stage 1 sleep, and stage 2 sleep, respectively.

Transitions from one sleep stage to another sleep stage may be identified by distinct characteristics associated with each stage of a sleep cycle. For example, stage 1 sleep may be identified based on the presence of hypnic jerks (e.g., involuntary twitching of muscles). The accelerometer 148 may be placed on a limp of the patient 102 to detect body movements associated with hypnic jerks. The sensor data collection system 106 may collect the accelerometer data from the accelerometer 148. The IMD 104 and/or the sensor data collection system 106 may analyze the accelerometer data to determine whether the patient 102 is in stage 1 sleep or has transitioned into stage 1 sleep. A first particular number of occurrences of the hypnic jerks (e.g., a threshold number during a particular time period) may indicate that the patient 102 has transitioned from wakefulness to stage 1 sleep. Consistent occurrences of hypnic jerks may indicate that the patient 102 is in stage 1 sleep.

Stage 2 sleep may be identified based on a decrease in body movements (e.g., a decrease in frequency of body movements, a decrease in frequency of hypnic jerks, and/or absence of hypnic jerks) relative to the body movements in stage 1 sleep, the presence of sleep spindles (e.g., bursts of oscillatory brain activities with frequencies approximately between 12 Hz to 14 Hz and a duration of approximately at least 0.5 second), and/or the presence of relatively stable heart rates. The decrease in body movements may be identified from the accelerometer data and/or EMG data. The EMG sensor 146 may be placed on the torso of the patient 102. Because the presence of hypnic jerks may indicate that the patient 102 is in stage 1 sleep, a period of no registered body movements or a decrease in frequency of body movements following the presence of hypnic jerks may indicate that the patient 102 has transitioned from stage 1 sleep to stage 2 sleep. Snoring may also be an indicator of stage 2 sleep which can be measured by either an accelerometer signal, respiration sensor placed on the torso or on the nose, an impedance monitoring unit, or a combination thereof.

In addition or alternatively, the EEG sensor 140 may be placed on the head of the patient 102 to detect brain electrical activity of the patient 102. The IMD 104 and/or the sensor data collection system 106 may analyze the EEG data (e.g., the brain electrical activities the patient 102) to determine whether the patient 102 is in stage 2 sleep or has transitioned into stage 2 sleep based on the presence of sleep spindles. A first particular number of occurrences of the sleep spindles may indicate that the patient 102 has transitioned from stage 1 sleep to stage 2 sleep. Consistent occurrences of the sleep spindles may indicate that the patient 102 is in stage 2 sleep.

In addition or alternatively, the ECG sensor 144 may be placed on the torso of the patient 102 (e.g., near the chest of the patient 102) to detect electrical activities of the heart of the patient 102. The IMD 104 and/or the sensor data collection system 106 may analyze the ECG data (e.g., the electrical activities of the heart of the patient 102) to determine whether the patient 102 is in stage 2 sleep or has transitioned into stage 2 sleep. A first particular number of occurrences of orderly ECG patterns (e.g., a threshold number during a particular duration) may indicate that the patient 102 has transitioned from stage 1 sleep to stage 2 sleep. Consistent occurrences of the orderly ECG patterns may indicate that the patient 102 is in stage 2 sleep. Stage 1 sleep and stage 2 sleep are considered light sleep stages.

Stage 3 sleep may be identified based on an increase in body movements relative to the body movements of the patient 102 in stage 2 sleep and/or a decrease in frequency of electrical activities of the brain of the patient 102. The IMD 104 and/or the sensor data collection system 106 may analyze the accelerometer data, the EMG data, and/or the EEG data to determine whether the patient 102 is in stage 3 sleep. The increase in body movements may be identified using the accelerometer data and/or the EMG data. A first particular number of occurrences of increased body movements (e.g., a threshold number during a particular duration) may indicate that the patient 102 has transitioned from stage 2 sleep to stage 3 sleep. Consistent occurrences of the increased body movements relative to the body movements in stage 2 sleep may indicate that the patient 102 is in stage 3 sleep. A first particular number of occurrences of brain electrical activities with a decreased frequency relative to the frequency of brain electrical activities in stage 2 sleep (e.g., 0.5 Hz-2 Hz in stage 3 sleep as compared to 12 Hz-14 Hz in stage 2 sleep) may indicate that the patient 102 has transitioned from stage 2 sleep to stage 3 sleep. Consistent occurrences of brain electrical activities with a decreased frequency relative to the frequency of brain electrical activities in stage 2 sleep may indicate that the patient 102 is in stage 3 sleep. Also, a decrease in snoring from stage 2 sleep may be an indicator of stage 3 sleep. Stage 3 sleep is considered a deep sleep stage.

REM stage sleep may be identified based on an increase in eye movements of the patient 102 relative to the eye movements of the patient 102 in stage 3 and/or a decrease in body movements of the patient 102 relative to the body movements of the patient 102 in stage 3. The EOG sensor 142 may be placed near the eyes of the patient 102 to detect the eye movements of the patient 102. The IMD 104 and/or the sensor data collection system 106 may analyze the EOG data and/or the accelerometer data to determine whether the patient 102 is in REM stage sleep. A first particular number of occurrences of eye movements with an increased frequency relative to the eye movements in stage 3 (e.g., a threshold number during a particular duration) may indicate that the patient 102 has transitioned from stage 3 sleep to REM stage sleep. Consistent occurrences of eye movements with an increased frequency relative to the frequency of the eye movements in stage 3 sleep may indicate that the patient 102 is in REM stage sleep. In addition, a decrease in snoring from stage 3 sleep, or the absence of snoring may be an indicator of REM stage sleep. Generally, snoring is more prominent in the light sleep stages (e.g., stage 1 sleep and stage 2 sleep), decreases during deep sleep (e.g., stage 3 sleep), and further decreases and may be absent during REM stage sleep. Exceptions to this snoring pattern may apply to patients with certain disorders (e.g., sleep apnea).

When the patient 102 transitions from a sleep stage to wakefulness, such a transition may be detected based on an increase in heart rate relative to a heart rate of the patient 102 in the sleep stage via the ECG data, an increase in a frequency of the brain electrical activities relative to a frequency of the brain electrical activities of the patient 102 in the sleep stage via the EEG data, and an increase in body movement relative to the body movements of the patient 102 in the sleep stage via the accelerometer data, the EMG data, or a combination thereof. Sleep stage determination sensitivity and specificity may be increased by using multiple sensors. For example, the combination of ECG, EEG, and accelerometer may provide a more accurate indication of a current sleep stage that any one of those sensor types alone.

In a particular embodiment, the sensor data collection system 106 determines the sleep cycle information based on the body parameter data and also determines CNS adjustment data based on the sleep cycle information. The sensor data collection system 106 transmits the CNS adjustment data to the IMD 104. The IMD 104 adjusts one or more CNS parameters based on the CNS adjustment data. In a particular embodiment, the IMD 104 or the sensor data collection system 106 determines an efficacy of a CNS therapy based on a comparison of sleep cycle information of the patient 102 before a CNS therapy and sleep cycle information of the patient 102 during and/or after the CNS therapy. For example, the IMD 104 or the sensor data collection system 106 may compare a first sleep quota of the patient 102 before a CNS therapy to a second sleep quota of the patient 102 after the CNS therapy. As another example, the IMD 104 or the sensor data collection system 106 may compare the second sleep quota to a threshold. The system 100 may improve sleep quality of the patient 102 and may reduce seizures that the patient 102 experiences during sleep.

In addition to adjusting CNS parameters based on sleep cycle information, a seizure detection algorithm may be adjusted based on the sleep cycle information. One or more parameters of a seizure detection algorithm may be adjusted based on a current sleep stage, sleep stage transition, an amount of time spent in a particular sleep stage, probability of a seizure occurring in a current stage, a patient's sleep history, other sleep cycle information, or a combination thereof. In some embodiments, the one or more parameters of the seizure detection algorithm may be adjusted to increase seizure detection sensitivity when the current sleep stage is stage 2 sleep, as a seizure is more likely to occur in stage 2 sleep than in stage 3 sleep and REM stage sleep. Certain parameters may be adjusted to be more sensitive while others may be adjusted to be less sensitive depending on the sleep stage. For example, the seizure detection algorithm may adjust detection parameters associated with the accelerometer to distinguish hypnic jerks from a seizure. The seizure detection algorithm may be adjusted to be less sensitive to the accelerometer during stage 1 sleep or additional processing of the accelerometer signal may be used to further distinguish, and filter out, hypnic jerks from movements characteristic of a seizure.

Figure 2A:
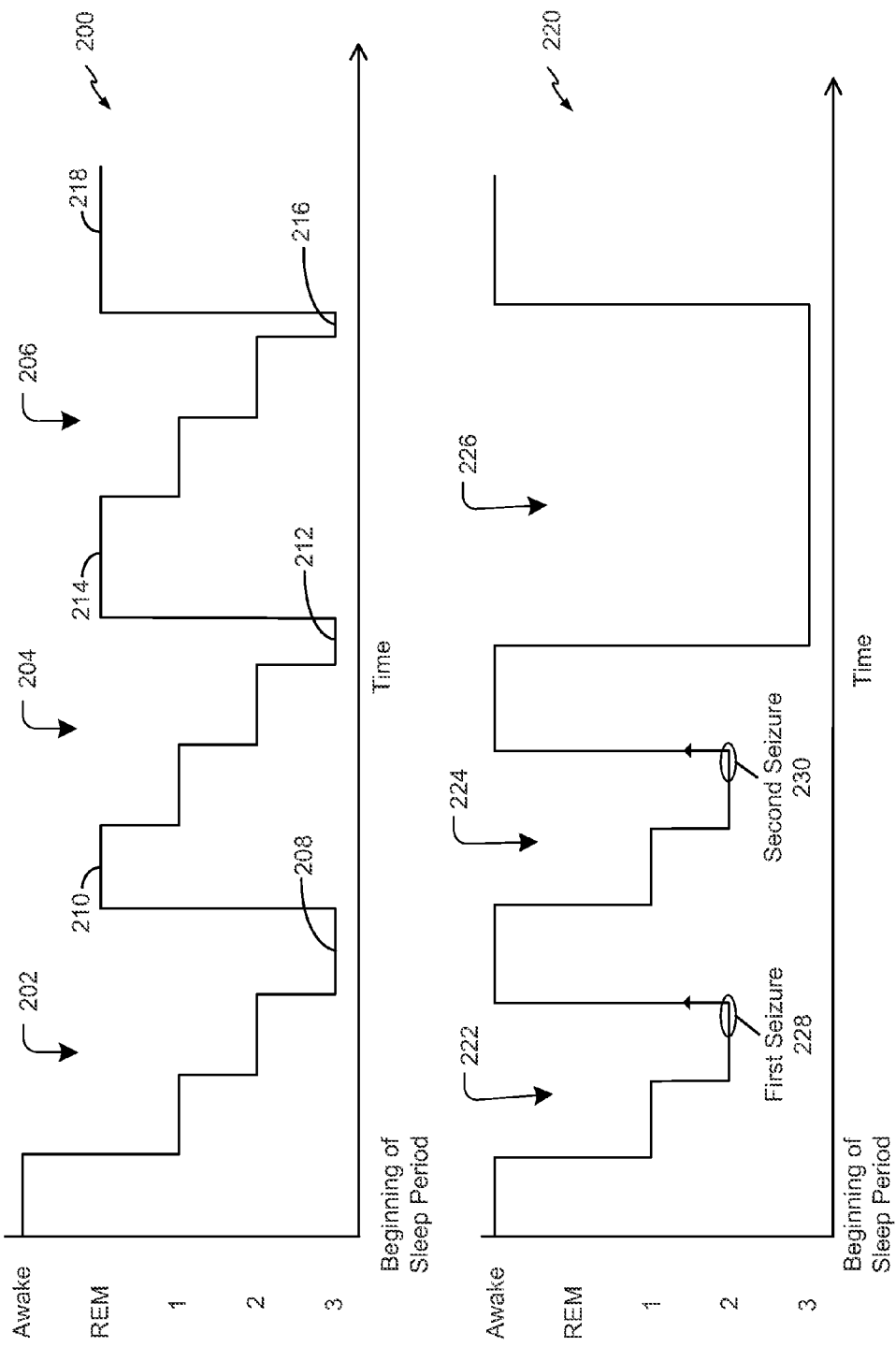
FIG. 2A is a diagram illustrating a sleep pattern when no seizures occur during sleep.

Referring to FIG. 2A, a diagram illustrating a sleep pattern 200 of a patient (e.g., the patient 102 of FIG. 1) when no seizures occur during sleep is shown according to an exemplary embodiment. The sleep pattern 200 may include a first sleep cycle 202, a second sleep cycle 204, and a third sleep cycle 206. During the first sleep cycle 202, the patient 102 may spend a first amount of time 208 in stage 3 sleep and may spend a second amount of time 210 in REM stage sleep. During the second sleep cycle 204, the patient 102 may spend a third amount of time 212 in stage 3 sleep and may spend a fourth amount of time 214 in REM stage sleep. The first amount of time 208 is typically a longer duration of time than the third amount of time 212. The second amount of time 210 is typically a shorter duration of time than the fourth amount of time 214. During the third sleep cycle 206, the patient 102 may spend a fifth amount of time 216 in stage 3 sleep and may spend a sixth amount of time 218 in REM stage sleep. The third amount of time 212 is typically a longer duration of time than the fifth amount of time 216. The fourth amount of time 214 is typically a shorter duration of time than the sixth amount of time 218. The sleep pattern 200 may illustrate that an amount of time spent in stage 3 sleep decreases as the patient 102 gets closer to completing a sleep period. The sleep pattern 200 may also illustrate that an amount of time spent in REM stage sleep increases as the patient 102 gets close to completing the sleep period.

FIG. 2A, also illustrates a diagram of a sleep pattern 220 of the patient 102 when seizures occur during sleep is shown according to an exemplary embodiment. The sleep pattern 220 may include a fourth sleep cycle 222, a fifth sleep cycle 224, and a sixth sleep cycle 226. During the fourth sleep cycle 222, the patient 102 experiences a first seizure 228 during stage 2 sleep and the patient 102 is awakened by the first seizure 228. Because the patient 102 is awakened before transitioning to stage 3 sleep, the patient 102 may not get any stage 3 sleep or REM stage sleep during the fourth sleep cycle 222. During the fifth sleep cycle 224, the patient 102 experiences a second seizure 230 during stage 2 sleep and the patient 102 is awakened by the second seizure 230. Because the patient 102 is awakened before transitioning to stage 3 sleep, the patient 102 may not get any stage 3 sleep or REM stage sleep during the fifth sleep cycle 24. During the sixth sleep cycle 226, the patient 102 may go directly into stage 3 sleep to compensate for the lack of stage 3 sleep, but may not get any stage 1, stage 2, and REM stage sleep. The sleep pattern 220 illustrates that seizures that occur during sleep may interfere with the sleep quality of the patient 102.

Figure 2B:
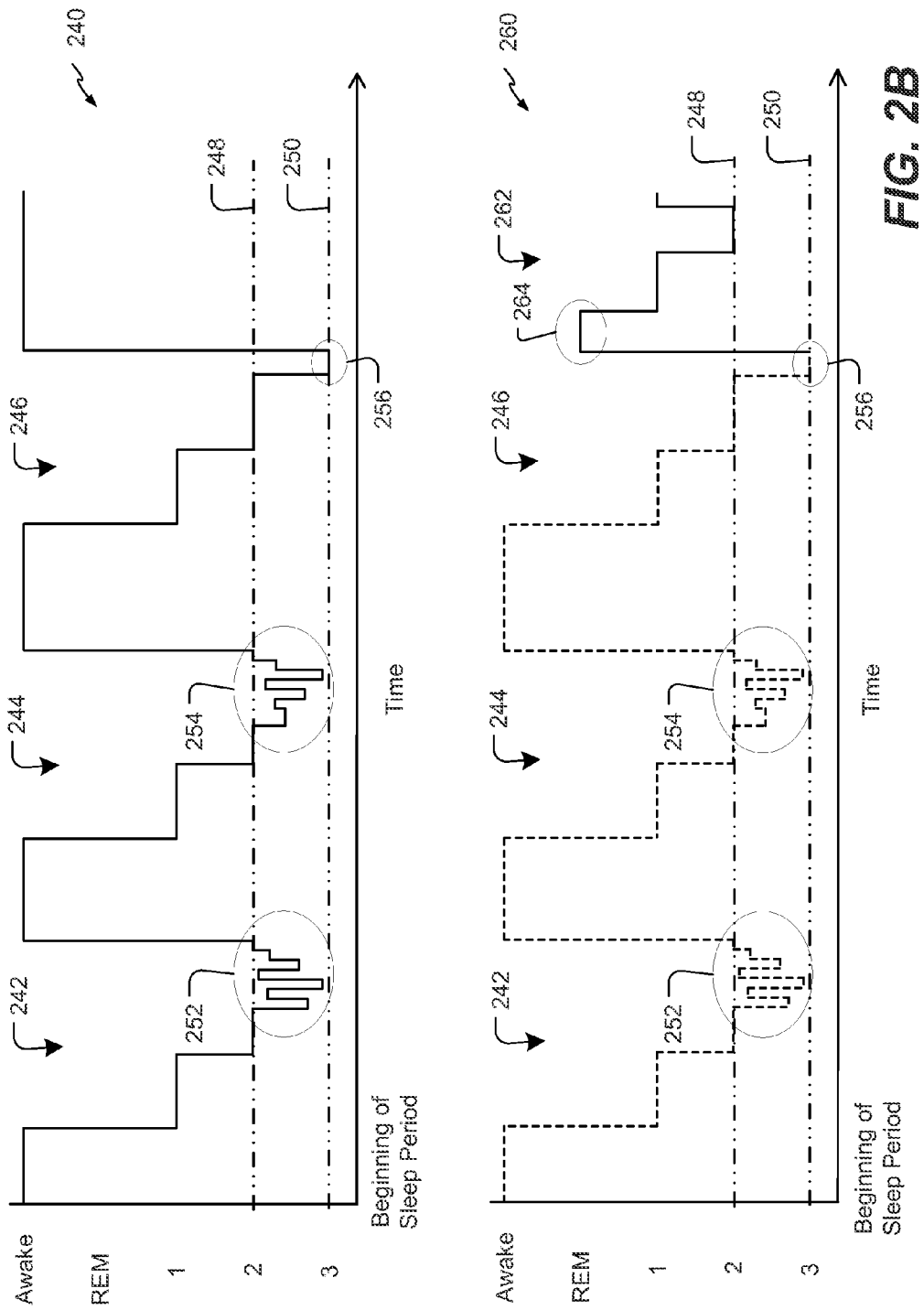
FIG. 2B is a diagram illustrating a sleep pattern when seizures occur during sleep.

Referring to FIG. 2B, a diagram illustrating a sleep pattern 240 of the patient 102 when no seizures occur during sleep is shown according to an exemplary embodiment. The sleep pattern 240 may include a seventh sleep cycle 242, an eighth sleep cycle 244, and a ninth sleep cycle 246. During the seventh sleep cycle 242 in stage 2 sleep 248 the patient 102 begins to vacillate at 252 between stage 2 sleep 248 and stage 3 sleep 250 never fully entering or remaining in stage 3 sleep 250 and then transitions to an awake state. During the eighth sleep cycle 244 the patient 102 again begins to vacillate at 254 between stage 2 sleep 248 and stage 3 sleep 250 never fully entering or remaining in stage 3 sleep 250 and then transitions to an awake state. During the ninth sleep cycle 246, the patient 102 successfully transitions from stage 2 sleep 248 to stage 3 sleep 250 and spends a fourth amount of time 256 in stage 3 sleep. However, the patient may then transition to an awake state before entering REM stage sleep. In this sleep pattern 240 the patient 102 gets little deep restorative stage 3 sleep only spending a fourth amount of time 256 in stage 3 sleep, and no REM sleep. In FIG. 2B, a sleep pattern 260 is illustrated having the same seventh sleep cycle 242, eighth sleep cycle 244, and stage 1 through 3 sleep of the ninth sleep cycle 246 as sleep pattern 240. In sleep pattern 260, the patient transitions to REM stage sleep in the ninth sleep cycle 246 and spends a fifth amount of time 264 in REM stage sleep and begins a tenth sleep cycle 262. In this sleep pattern 260 the patient 102 gets little deep restorative stage 3 sleep only spending a fourth amount of time 256 in stage 3 sleep, and little REM sleep spending only a fifth amount of time 264 on REM stage sleep.

Patients with neurological disorders, including epilepsy, often exhibit poor sleep architecture. Patients with epilepsy may experience periods in which their brain state is unstable, but does not arise to the level of a seizure. During sleep, these unstable periods may be more likely to occur during stage 2 sleep or the transition from stage 2 sleep to stage 3 sleep. In the unstable brain state, the patient may vacillate between stage 2 sleep and stage 3 sleep followed by an awake state. The lack of deep restorative stage 3 sleep and REM sleep may result in sleep deprivation and may aggravate or worsen the patient's epilepsy or other neurological condition.

Figure 3:
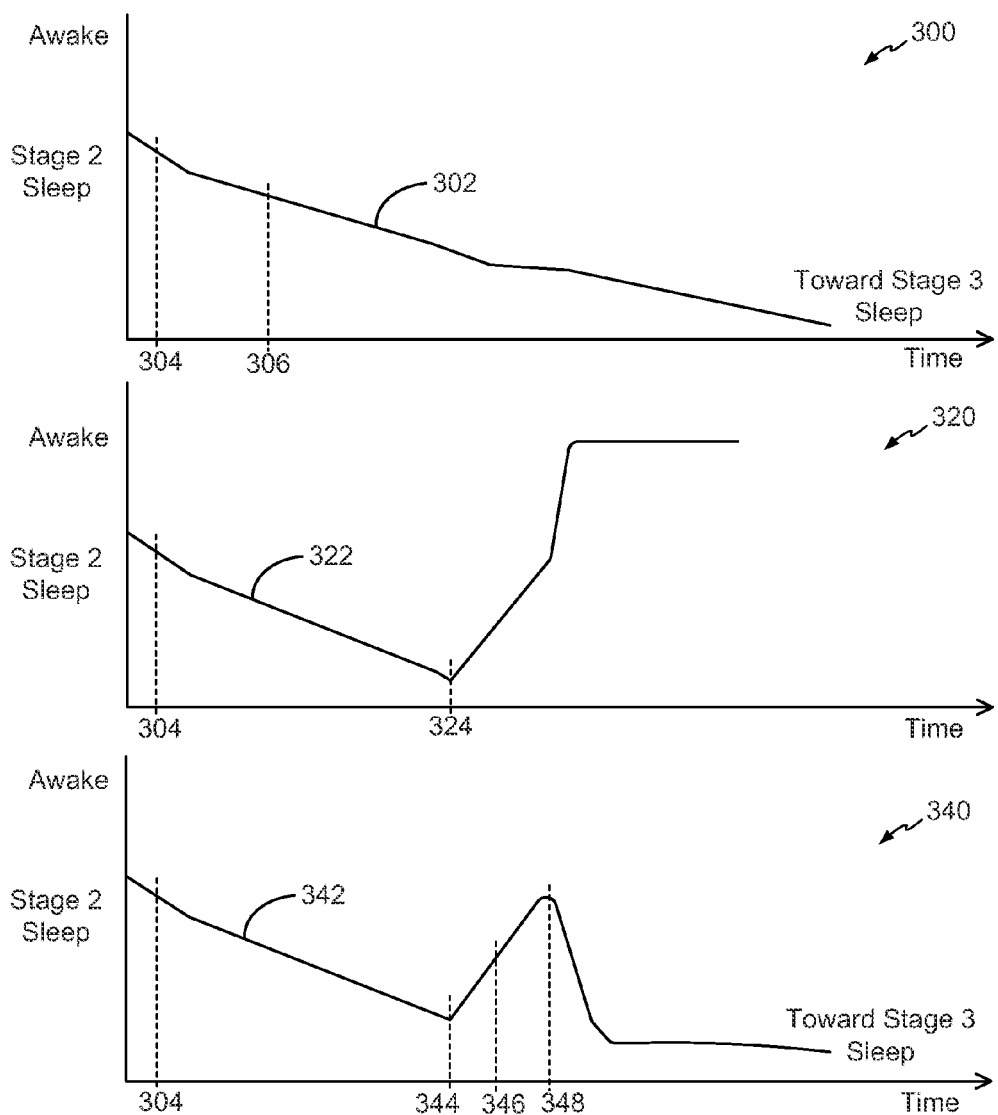
FIG. 3 is a diagram illustrating an effect of cranial nerve stimulation in a sleep stage.

Referring to FIG. 3, diagrams illustrating an effect of cranial nerve stimulation in a sleep stage are shown according to an exemplary embodiment. In diagram 300, line 302 represents an amount of time a patient (e.g., the patient 102 of FIG. 1) has spent in stage 2 sleep in a particular sleep cycle (e.g., as monitored by the IMD 104 of FIG. 1 or the sensor data collection system 106). In diagram 300, CNS may be adjusted and applied to help drive the patient toward stage 3 sleep when the sleep cycle information indicates a transition to stage 2 sleep at 304, a current sleep stage is stage 2 sleep, a predetermined amount of time 306 spent in stage 2 sleep during a sleep cycle, or a combination thereof. In some embodiments, a seizure or otherwise unstable brain state may be avoided by assisting the patient through stage 2 sleep to stage 3 sleep.

As illustrated in diagram 320, line 322 represents a patient's stage 2 sleep being interrupted by a seizure or an unstable brain state at 324. The patient may start transitioning at, or near, 324 from stage 2 sleep toward an awake state instead of remaining in stage 2 sleep.

In diagram 340, line 342 represents a patient's stage 2 sleep beginning to transition toward an awake state at 344 resulting from the onset of a seizure or an unstable brain state. Based on the sleep cycle information, the IMD 104 of FIG. 1 may identify the transition from stage 2 sleep toward wakefulness. In response to identifying the transition, the IMD 104 may adjust one or more CNS parameters to adjust the CNS applied to the patient 102 or may start applying CNS according to the adjusted one or more CNS parameters, at 346. The CNS may drive the patient 102 toward stage 3 sleep (e.g., remain in stage 2 sleep until the patient 102 has spent an amount of time in stage 2 sleep equal to the threshold 302). In response to receiving the CNS applied according to the one or more adjusted parameters, the patient 102 may remain or return to stage 2 sleep at 348 and continue toward stage 3 sleep.

Figure 4:
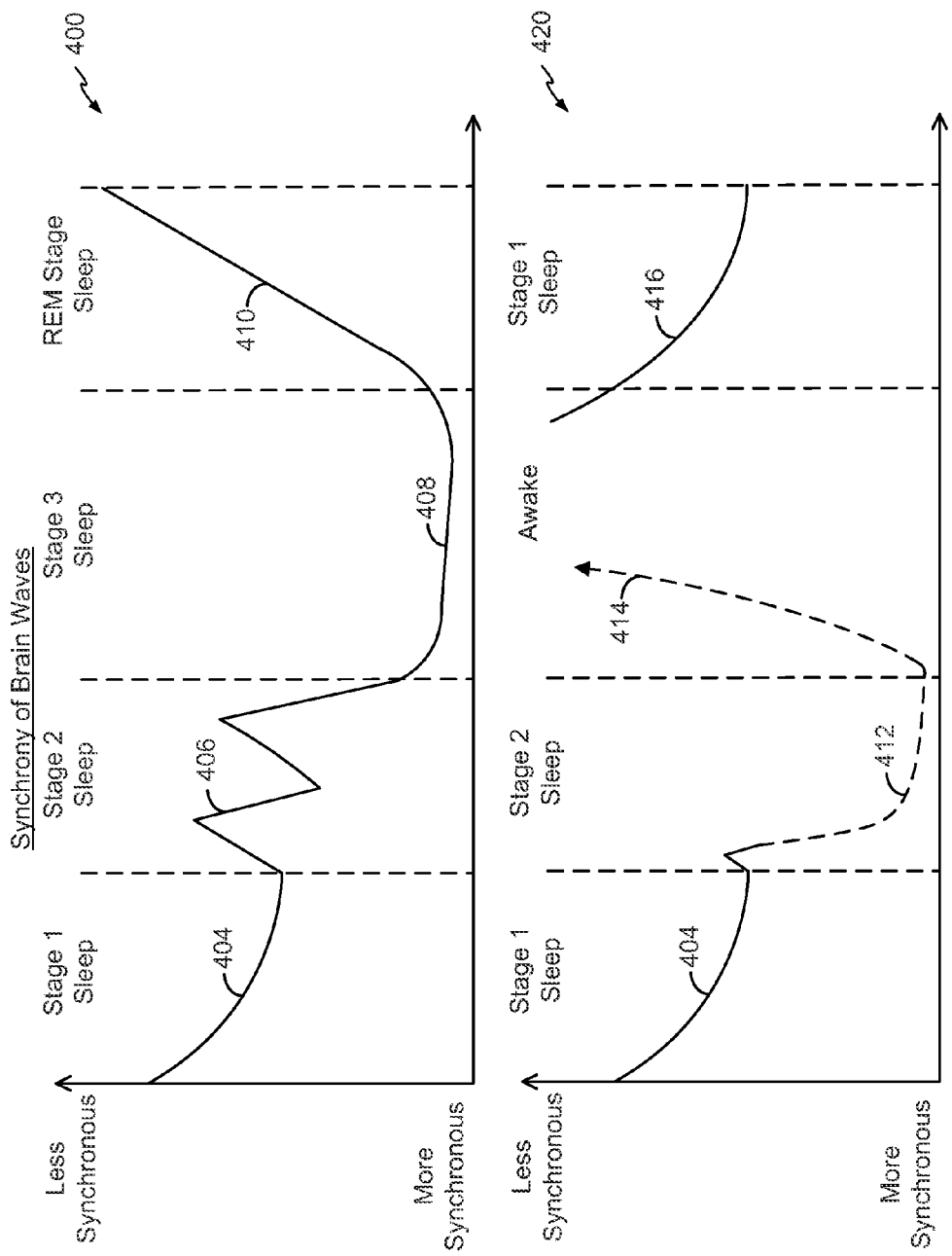
FIG. 4 is a diagram illustrating cranial nerve stimulation parameter adjustments based on sleep cycle information.

Referring to FIG. 4, a diagram 400 illustrating, in a simplified form, brain wave synchrony over time in various sleep stages is shown according to an exemplary embodiment. The diagram 400 may be a synchrony profile. The synchrony profile may indicate synchrony level changes in each sleep stage as measured by different EEG channels (e.g., different EEG probes) when no seizures occur during sleep. The diagram 400 may include a first segment 404, a second segment 406, a third segment 408, and a fourth segment 410. Synchrony of the brain waves may include synchrony of brain wave frequency as measured by the different EEG channels, synchrony of brain wave energy as measured by the different EEG channels, synchrony of brain wave stability as measured by the different EEG channels, synchrony of brain wave phase as measured by the different EEG channel, or a combination thereof. In addition, the change in synchrony of brain waves may also be measured within and/or across multiple EEG channels. Furthermore, the change in synchrony within and/or across multiple channels of different body parameters may also be measured.

As shown in FIG. 4, when a patient (e.g., the patient 102 of FIG. 1) is in stage 1 sleep, a synchrony of the brain waves may increase (i.e., become more synchronous) relative to a synchrony of the brain waves when the patient is awake, as indicated by the first segment 404. When the patient is in stage 2 sleep, a synchrony of the brain waves may fluctuate as indicated by the second segment 406. When the patient is in stage 3 sleep, a synchrony of the brain waves may increase relative to the synchrony of the brain waves in stage 2 sleep, as indicated by the third segment 408. When the patient is in REM stage sleep, a synchrony of the brain waves may decrease (i.e., become less synchronous) relative to the synchrony of the brain waves in stage 3 sleep, as indicated by the fourth segment 410.

In FIG. 4, a diagram 420 illustrating, in a simplified form, brain wave synchrony over time in various sleep stages, including the onset of a seizure or unstable brain state, is shown according to an exemplary embodiment. The seizure onset may be determined using other body parameters. During onset of a seizure or unstable brain state and without the CNS, instead of fluctuating in stage 2 sleep, the brain waves in stage 2 sleep may become more synchronous relative to the synchrony of the brain waves in stage 1 sleep, as indicated by a fifth segment 412. After the seizure or unstable brain state, the synchrony of the brain increases as the patient transitions to an awake state, as indicated by a sixth segment 414. The patient then transitions from an awake state to stage 1 sleep and the synchrony of the brain waves may increase (i.e., become more synchronous) relative to the synchrony of the brain waves when the patient is awake, as indicated by the seventh segment 416.

A medical device (e.g., the IMD 104 of FIG. 1) may monitor brain wave synchrony level changes of the patient 102 based on the sleep cycle information (e.g., the EEG data) to adjust one or more CNS parameters. The one or more CNS parameters may include a pulse width, an output current, a CNS frequency, a CNS duty cycle, a CNS on-time, a CNS off-time, a CNS frequency sweep, burst frequency, or a combination thereof. The one or more CNS parameters may be adjusted such that synchrony of the brain waves may substantially conform to the synchrony profile. For example, when the patient is in stage 2 sleep, the one or more CNS parameters may be adjusted such that synchrony of the brain waves may fluctuate (as in normal stage 2 sleep). As another example, when the patient is in stage 3 sleep, the one or more CNS parameters may be adjusted such that the synchrony may decrease (driving the patient toward REM stage sleep). One CNS parameter that may be used to affect the synchrony of the brain is frequency of stimulation pulses. For example, higher frequency stimulation pulses (e.g., 100 Hz or more, 100-200 Hz, 100-350 Hz) may have a desynchronizing affect while low frequency stimulation pulses (e.g., 30 Hz or less, 50 Hz or less, less than 100 Hz) may have a synchronizing effect. Therefore, low frequency stimulation pulses may be used to drive the patient from stage 1 sleep to stage 2 sleep and stage 2 sleep to stage 3 sleep while higher frequency stimulation pulses may be used to drive the patient from stage 3 sleep to REM stage sleep. As another example, the CNS may be vagus nerve stimulation (VNS) to stimulate the vagus nerve. Conventional VNS (e.g., pulse frequency of about 30 Hz, pulse width around 250-500 microseconds, on-time of about 30 sec, and an off-time of 5 minutes) may be used to drive the patient from stage 1 sleep to stage 2 sleep and stage 2 sleep to stage 3 sleep. Microburst VNS (e.g., pulse frequency of about 100-250 Hz, pulse width around 250-500 microseconds, 2-10 pulses per burst, an interburst interval of about 100 milliseconds to 1 second, a burst duration of 100 milliseconds or less) may be used to drive the patient from stage 3 sleep to REM stage sleep.

Figure 5A:
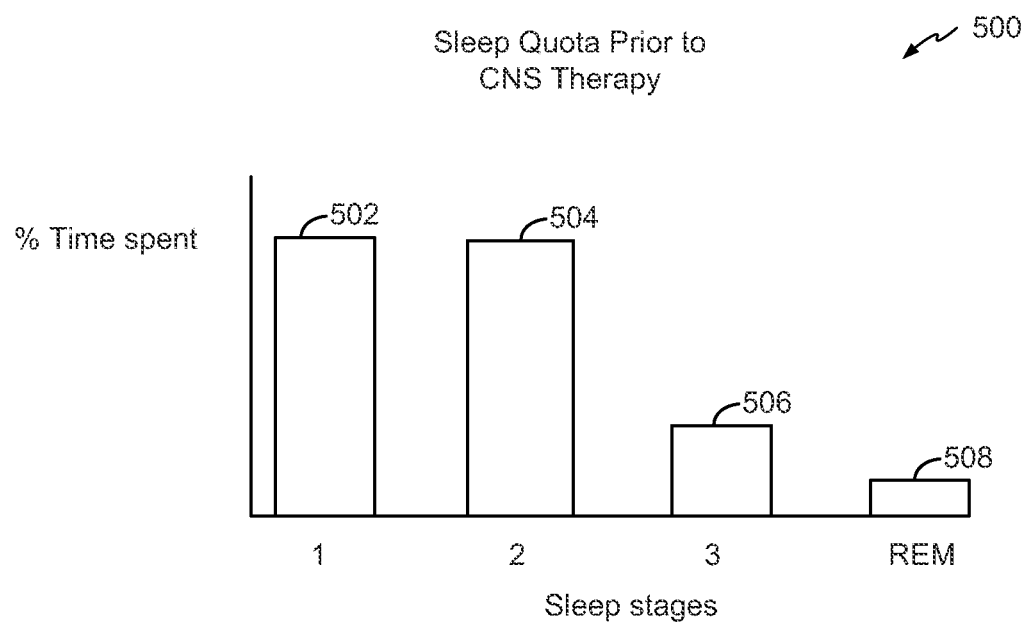
FIG. 5A is a diagram of a sleep quota of a patient before receiving cranial nerve stimulation.

Referring to FIG. 5A, a diagram of a first sleep quota 500 of a patient (e.g., the patient 102 of FIG. 1) with a seizure disorder before receiving CNS therapy to treat the seizure disorder is shown according to an exemplary embodiment. The first sleep quota 500 may include a first portion 502, a second portion 504, a third portion 506, and a fourth portion 508. The first sleep quota 500 may be a sleep quota of the patient when the patient experiences seizures during sleep. The first portion 502 may correspond to an accumulative amount of time the patient spent in stage 1 sleep in a first sleep period (e.g., a night) before receiving the CNS therapy. The first sleep period may include one or more sleep cycles. The second portion 504 may correspond to an accumulative amount of time the patient spent in stage 2 sleep in the first sleep period. The third portion 506 may correspond to an accumulative amount of time the patient spent in stage 3 sleep in the first sleep period. The fourth portion 508 may correspond to an accumulative amount of time the patient spent in REM stage sleep in the first sleep period.

Figure 5B:
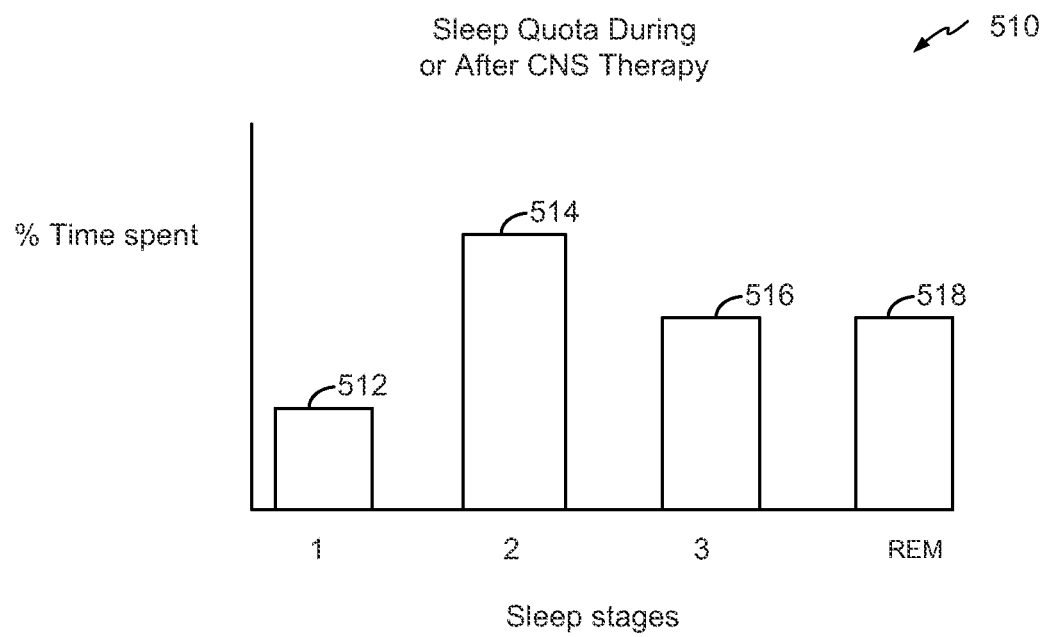
FIG. 5B is a diagram of a sleep quota of the patient of FIG. 5A after receiving cranial nerve stimulation.

Referring to FIG. 5B, a diagram of a second sleep quota 510 of the patient of FIG. 5A after receiving the CNS therapy to treat the seizure disorder is shown according to an exemplary embodiment. The second sleep quota 510 may include a fifth portion 512, a sixth portion 514, a seventh portion 516, and an eighth portion 518. The fifth portion 512 may correspond to an accumulative amount of time the patient spent in stage 1 sleep in a second sleep period (e.g., a night) during the CNS therapy or after the CNS therapy (while recovering). The second sleep period may include multiple sleep cycles. The sixth portion 514 may correspond to an accumulative amount of time the patient spent in stage 2 sleep in the second sleep period. The third portion 506 may correspond to an accumulative amount of time the patient spent in stage 3 sleep in the second sleep period. The fourth portion 508 may correspond to an accumulative amount of time the patient spent in REM stage sleep in the second sleep period.

Information regarding efficacy of the CNS therapy may be determined based on a comparison of the first sleep quota 500 to the second sleep quota 510 (e.g., via the IMD 104 of FIG. 1). A result of the comparison may indicate that the seventh portion 516 is greater than the third portion 506 and the eighth portion 518 is greater than the fourth portion 508. Thus, the comparison may indicate that the patient spends more time in stage 3 sleep and REM stage sleep during or after the CNS therapy. The increase of time the patient spends in stage 3 sleep and REM stage sleep may indicate that the CNS is effective in treating a particular disorder. For example, when the CNS therapy is to treat one or more seizure disorders, the comparison may indicate that the CNS therapy is effective in treating the seizure orders. In a particular embodiment, the first sleep quota 500 and/or the second sleep quota 510 may be compared to a threshold to determine a degree of efficacy. For example, a threshold of REM stage sleep may correspond to a particular amount of time that a healthy person spends in REM stage sleep in a sleep cycle and/or a sleep period. The fourth portion 508 and the eighth portion 518 may be compared to the threshold to determine an amount of improvement (e.g., how much more time the patient spends in REM stage sleep) as a measure of the efficacy.

The information regarding efficacy of the CNS therapy and/or the degree of efficacy may be determined by the IMD 104 of FIG. 1, the sensor data collection system 106, the external programming device 108, the external computing device 160, or a combination thereof. The IMD 104, the sensor data collection system 106, the external programming device 108, the external computing device 160, or a combination thereof, may generate a recommendation (e.g., via a report) regarding adjustments that can be made to improve the efficacy based on the information regarding efficacy of the CNS therapy and/or the degree of efficacy.

The IMD 104, the sensor data collection system 106, the external programming device 108, the external computing device 160, or a combination thereof, may communicate the information regarding efficacy of the CNS therapy and/or the degree of efficacy to the patient, to a health care provider, or a combination thereof. For example, the IMD 104, the sensor data collection system 106, the external programming device 108, the external computing device 160, or a combination thereof, may generate a report that includes the information regarding the efficacy of the CNS therapy and/or the degree of efficacy, may show the information regarding efficacy of the CNS therapy and/or the degree of efficacy via a display, etc. The IMD 104, the sensor data collection system 106, the external programming device 108, the external computing device 160, or a combination thereof, may adjust one or more CNS parameters based on the information regarding the efficacy of the CNS therapy and/or the degree of efficacy.

Figure 6:
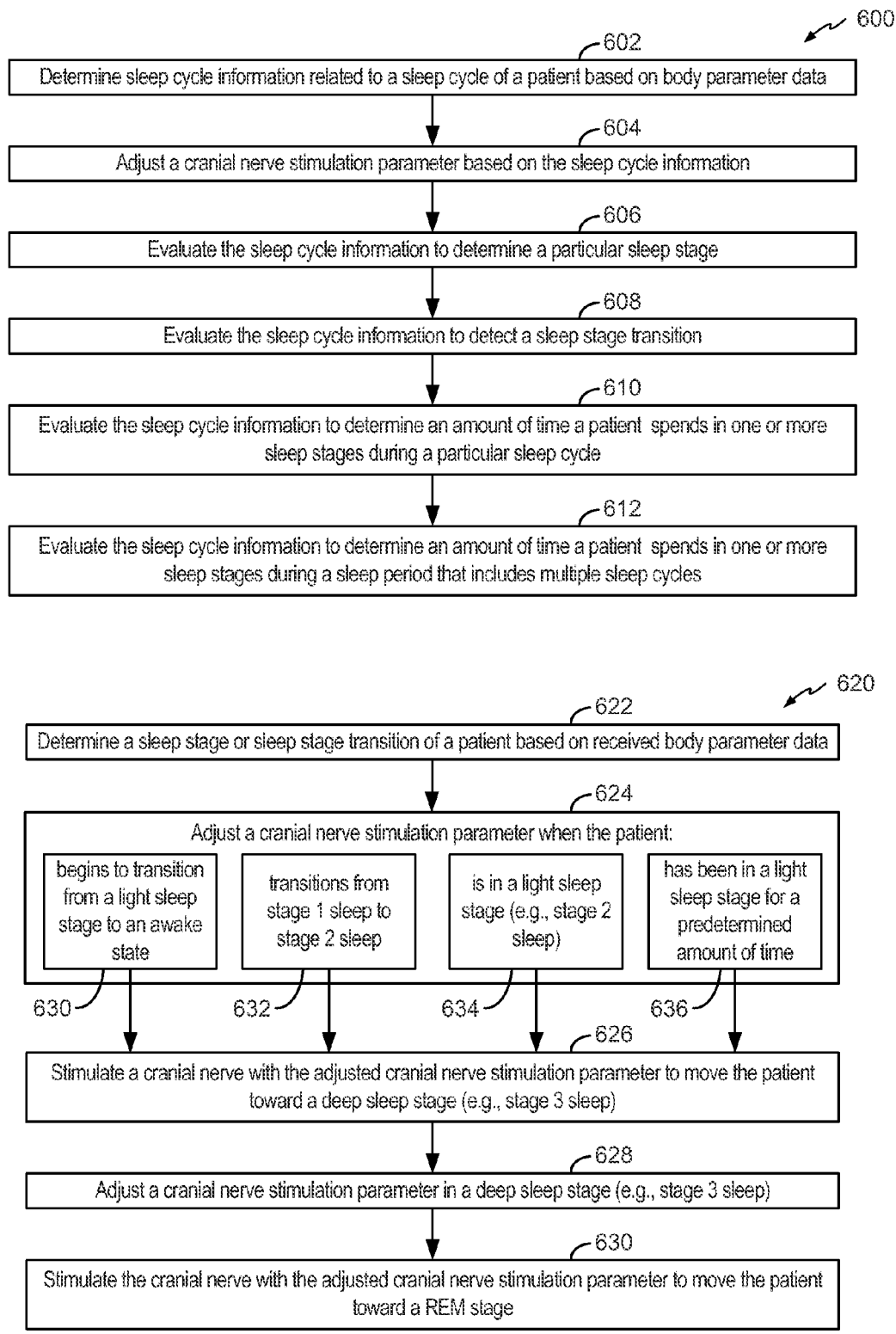
FIG. 6 is a flow chart of a first particular embodiment of a method of operation of a medical device associated with a cranial nerve stimulation therapy to treat seizures during sleep.

Referring to FIG. 6, a flow chart of a method 600 of operation of a medical device, such as the IMD 104 of FIG. 1, the sensor data collection system 106, the external programming device 108, the external computing device 160, or a combination thereof, associated with a cranial nerve stimulation therapy to treat seizures during sleep is shown according to an exemplary embodiment. The method 600 includes determining sleep cycle information related to a sleep cycle of a patient based on body parameter data, at 602. For example, referring to FIG. 1, based on the body parameter data, the IMD 104 may determine sleep cycle information related to a sleep cycle of the patient 102. The method 600 may also include adjusting a cranial stimulation parameter based on the sleep cycle information, at 604. For example, referring to FIG. 1, based on the sleep cycle information, the IMD 104 may adjust one or more CNS parameters to adjust the CNS applied to the patient 102. The one or more CNS parameters may include a pulse width, an output current, a CNS frequency, a CNS duty cycle, a particular nerve or nerves stimulated, a CNS frequency sweep, a CNS on-time, a CNS off-time, a CNS burst stimulation, or a combination thereof. As another example, referring to FIG. 4, the IMD 104 may also, or in the alternative, affect a synchrony of brain waves by adjusting the one or more CNS parameters to drive the patient through each stage of a sleep cycle, or from one sleep stage to another, to reduce seizure onsets based on the sleep cycle information.

Figure 8:
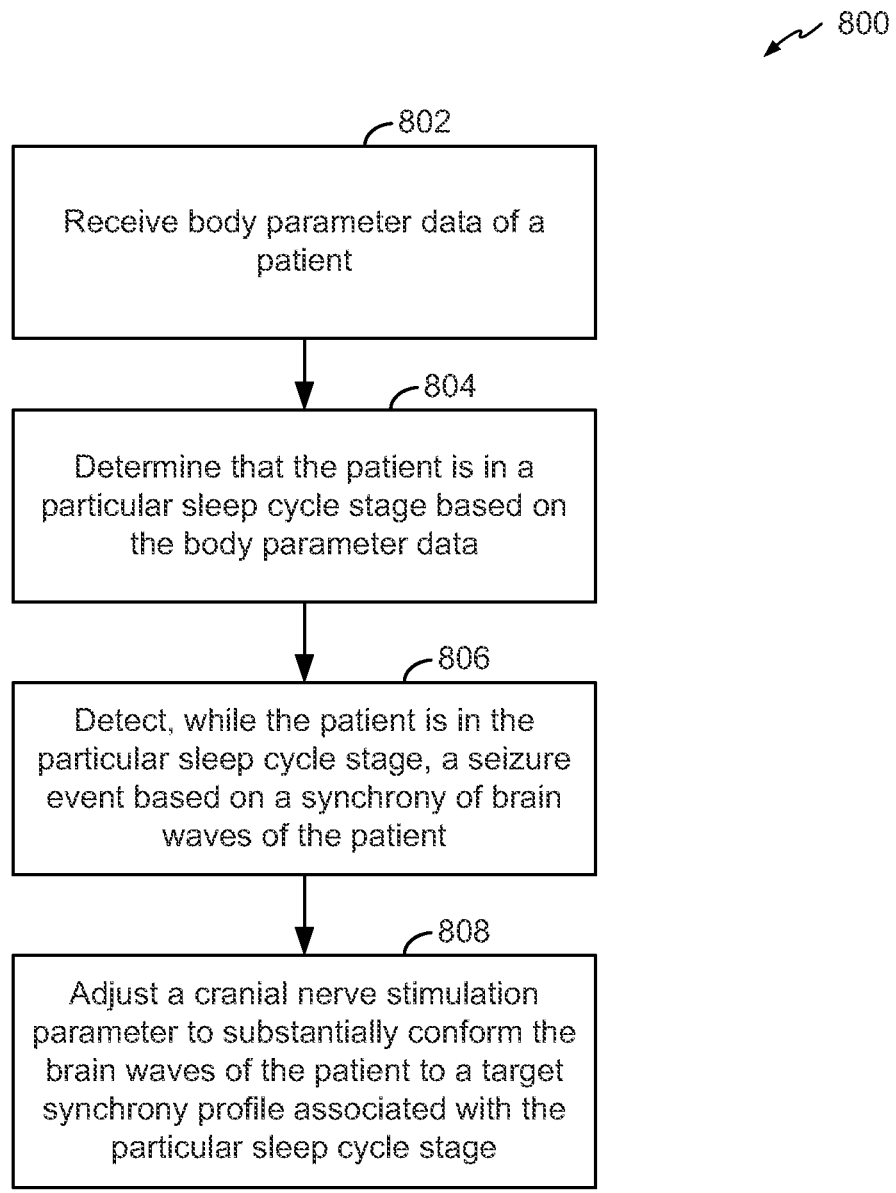
FIG. 8 is a flow chart of a third particular embodiment of a method of operation of a medical device associated with a cranial nerve stimulation therapy to treat seizures during sleep.

FIG. 8 is a flow chart of a third particular embodiment of a method of operation of a medical device to treat seizures during sleep. The method 800 includes receiving body parameter data of a patient, at 802. For example, referring to FIG. 1, the IMD 104 may receive body parameter data of the patient 102. The method 800 also includes determining that the patient is in a particular sleep cycle stage based on the body parameter data, at 804. For example, referring to FIG. 1, the IMD 104 may determine that the patient 102 is in a particular sleep cycle stage. As an illustrative non-limiting example, the IMD 104 may determine that the patient is in stage 2 sleep. The method 800 further includes detecting, while the patient is in the particular sleep cycle stage, a seizure event based on a synchrony of brain waves of the patient, at 806. For example, as shown at 412 of FIG. 4, an onset of a seizure event may be detected while the patient is in stage 2 sleep. The method 800 includes adjusting a cranial nerve stimulation parameter to substantially conform the brain waves of the patient to a target synchrony profile associated with the particular sleep cycle stage, at 808. For example, referring to FIG. 4, a cranial nerve stimulation parameter may be adjusted to increase synchrony of the brain waves of the patient to substantially conform the brain waves to the stage 2 segment 406.

In a particular embodiment, the method 600 further includes evaluating the sleep cycle information to determine a particular sleep stage, at 606. For example, referring to FIG. 1, the IMD 104, the sensor data collection system 106, the external programming device 108, the external computing device 160, or a combination thereof, may evaluate the sleep cycle information to determine a sleep stage of the patient. In a particular embodiment, the method 600 further includes evaluating the sleep cycle information to detect a sleep stage transition, at 608. For example, referring to FIG. 1, the IMD 104, the sensor data collection system 106, the external programming device 108, the external computing device 160, or a combination thereof, may evaluate the sleep cycle information to detect a sleep stage transition.

In a particular embodiment, the method 600 further includes evaluating the sleep cycle information to determine an amount of time the patient spends in one or more sleep stages during a particular sleep cycle, at 610. For example, referring to FIG. 1, the IMD 104, the sensor data collection system 106, the external programming device 108, the external computing device 160, or a combination thereof, may evaluate the sleep cycle information to determine an amount of time the patient 102 spends in one or more sleep stages during a particular sleep cycle. In a particular embodiment, the method 600 further includes evaluating the sleep cycle information to determine an amount of time the patient spends in one or more sleep stages during a sleep period that includes multiple sleep cycles, at 612. For example, referring to FIG. 1, the IMD 104, the sensor data collection system 106, the external programming device 108, the external computing device 160, or a combination thereof, may evaluate the sleep cycle information to an amount of time the patient 102 spends in one or more sleep stages during a sleep period that includes multiple sleep cycles.

Thus, the method 600 may enable a medical device to gather and evaluate patient information through each stage of a sleep cycle. Completing a sleep cycle may improve sleep quality of the patient and may reduce seizure onsets.

Referring again to FIG. 6, a flow chart of a method 620 of operation of a medical device, such as the IMD 104 of FIG. 1, associated with a cranial nerve stimulation therapy is shown according to an exemplary embodiment. The method 620 includes determining a sleep stage or sleep stage transition of a patient based on body parameter data, at 622. For example, referring to FIG. 1, based on the body parameter data, the IMD 104 may determine a sleep stage or sleep stage transition of the patient 102. The method 620 may also include adjusting a cranial stimulation parameter, at 624. The adjustment may be made for a variety of reasons depending on the patients sleep architecture. For example, referring to FIGS. 1 and 6, the IMD 104 may adjust the CNS parameter such that the CNS may drive the patient 102 toward deep sleep (e.g., stage 3 sleep) when the patient: begins to transition from a light sleep stage (e.g., stage 2 sleep) to an awake state, at 630; transitions from stage 1 sleep to stage 2 sleep, at 632; is in a light sleep stage (e.g., stage 2 sleep), at 634; has been in a light sleep state (e.g., stage 2 sleep) for a predetermined amount of time 636; or a combination thereof. After the cranial nerve stimulation parameter is adjusted, the method 620 may further include stimulating a cranial nerve (e.g., vagus nerve, trigeminal nerve, hypoglossal nerve, glossopharyngeal nerve, or a combination thereof) with the adjusted parameter to move the patient toward a deep sleep stage (e.g., stage 3 sleep), at 626. In the deep sleep stage (e.g., sleep stage 3), the method 620 may further include adjusting a cranial nerve stimulation parameter, at 628, and stimulating the cranial nerve with the adjusted cranial nerve stimulation parameter to move the patient toward a REM stage, at 630. The synchrony of brain waves may be affected by adjusting the one or more CNS parameters to drive the patient from light sleep to deep sleep and from deep sleep to REM. Driving the patient in and/or through the sleep stages may improve the patient's sleep architecture and neurologic condition. For example, applying CNS with parameters adjusted based on sleep cycle information may reduce the number of seizures or unstable brain states the patient experiences during sleep. In addition, improved sleep quality may reduce the number of seizures or unstable brain states during periods in which the patient is awake.

Figure 7:
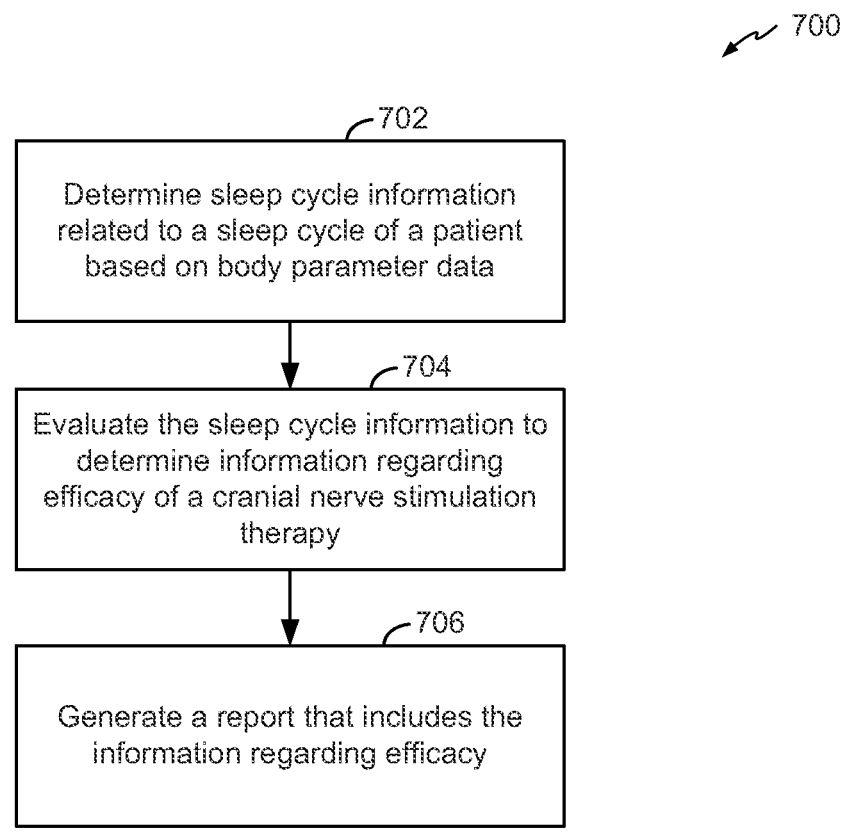
FIG. 7 is a flow chart of a second particular embodiment of a method of operation of a medical device associated with a cranial nerve stimulation therapy to treat seizures during sleep.

FIG. 7 is a flow chart of a second particular embodiment of a method of operation of a medical device, such as the IMD 104 of FIG. 1, the sensor data collection system 106, the external programming device 108, the external computing device 160, or a combination thereof, associated with a cranial nerve stimulation therapy to treat seizures during sleep according to an exemplary embodiment. The method 700 includes determining sleep cycle information related to a sleep cycle of a patient based on body parameter data, at 702. For example, referring to FIG. 1, based on the body parameter data, the IMD 104 may determine sleep cycle information related to a sleep cycle of the patient 102. The method 700 also includes evaluating the sleep cycle information to determine information regarding efficacy of a cranial nerve stimulation therapy, at 704. For example, referring to FIG. 5, the information regarding efficacy of the CNS therapy may be determined based on a comparison of the first sleep quota 500 to the second sleep quota 510. The method 700 further includes generating a report that includes the information regarding efficacy, at 706. For example, referring to FIG. 5, the IMD 104, the sensor data collection system 106, the external programming device 108, the external computing device 160, or a combination thereof, may generate a report that includes information regarding efficacy of the CNS therapy and/or the degree of efficacy. Thus, the method 700 may enable determination of information regarding efficacy of a therapy. Determining efficacy of a therapy may enable adjustment of the therapy to improve the efficacy.

Although the description above contains many specificities, these specificities are utilized to illustrate some of the exemplary embodiments of this disclosure and should not be construed as limiting the scope of the disclosure. The scope of this disclosure should be determined by the claims, their legal equivalents. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments that implement the systems and methods of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system.

As noted above, embodiments within the scope of the present disclosure include program products comprising computer readable storage device, or machine-readable media for carrying, or having machine-executable instructions or data structures stored thereon. Such machine-readable media can be any available media which can be accessed by a general purpose or special purpose computer or other machine with a processor. By way of example, such machine-readable media can comprise RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing descriptions of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A method comprising:
    receiving, at a computing device, body parameter data of a patient;
    retermining that the patient is in a particular preselected sleep cycle stage based on the body parameter data;
    detecting, while the patient is in the particular sleep cycle stage, a seizure event based on synchrony of brain waves of the patient; and
    adjusting, at the computing device, a cranial nerve stimulation parameter to substantially confirm the brain waves of the patient to a target synchrony profile associated with the particular sleep cycle stage.

2. The method of claim 1, wherein the body parameter data comprises electroencephalography (EEG) data, electrooculography (EOG) data, electromyography (EMG) data, electrocardiography (ECG) data, accelerometer data, or a combination thereof.

3. The method of claim 1, wherein the particular sleep cycle stage is determined further based on a sleep stage transition, an amount of time the patient spends in one or more stages during the particular sleep cycle, an amount of time the patient spends in one or more stages during a sleep period that includes multiple sleep cycles, or a combination thereof.

4. The method of claim 1,
    wherein the body parameter data is received from a sensor that is attached to the patient.

5. The method of claim 1, further comprising readjusting the cranial nerve stimulation parameter in association with a first transition from a light sleep stage to an awake state; a second transition from stage 1 sleep to stage 2 sleep; the patient being in the light sleep stage; the patient being in the light sleep stage for a particular amount of time; or a combination thereof.

6. The method of claim 5, further comprising stimulating a cranial nerve based on the readjusted cranial nerve stimulation parameter to drive the patient toward a deep sleep stage.

7. The method of claim 1, further comprising applying stimulation signals to a vagus nerve or a trigeminal nerve of the patient via a therapy delivery unit based on the adjusted cranial nerve stimulation parameter.

8. The method of claim 1, wherein the cranial nerve stimulation parameter indicates a pulse width, an output current, a cranial nerve stimulation frequency, a cranial nerve stimulation duty cycle, a particular nerve or nerves stimulated, a cranial nerve stimulation frequency sweep, a cranial nerve stimulation on-time, a cranial nerve stimulation off-time, or a combination thereof.

9. The method of claim 1, wherein the seizure event corresponds to an epileptic seizure.

* * * * *